United States Patent
Tomchuck et al.

(10) Patent No.: US 10,472,647 B2
(45) Date of Patent: Nov. 12, 2019

(54) PRIMARY MESENCHYMAL STEM CELLS AS A VACCINE PLATFORM

(71) Applicant: The Administrators of the Tulane Educational Fund, New Orleans, LA (US)

(72) Inventors: Suzanne L. Tomchuck, Memphis, TN (US); Elizabeth B. Norton, New Orleans, LA (US); Robert F. Garry, New Orleans, LA (US); Bruce Bunnell, Mandeville, LA (US); John D. Clements, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 452 days.

(21) Appl. No.: 14/081,740

(22) Filed: Nov. 15, 2013

(65) Prior Publication Data

US 2014/0178422 A1    Jun. 26, 2014

Related U.S. Application Data

(60) Provisional application No. 61/773,546, filed on Mar. 6, 2013, provisional application No. 61/745,156, filed on Dec. 21, 2012.

(51) Int. Cl.
*C12N 15/85* (2006.01)
*A61K 39/12* (2006.01)
*A61K 39/00* (2006.01)

(52) U.S. Cl.
CPC .............. *C12N 15/85* (2013.01); *A61K 39/12* (2013.01); *A61K 2039/5156* (2013.01); *C12N 2740/16134* (2013.01); *Y02A 50/388* (2018.01); *Y02A 50/39* (2018.01); *Y02A 50/394* (2018.01); *Y02A 50/396* (2018.01); *Y02A 50/403* (2018.01); *Y02A 50/407* (2018.01); *Y02A 50/41* (2018.01); *Y02A 50/412* (2018.01); *Y02A 50/421* (2018.01); *Y02A 50/423* (2018.01); *Y02A 50/466* (2018.01); *Y02A 50/469* (2018.01); *Y02A 50/478* (2018.01); *Y02A 50/484* (2018.01); *Y02A 50/487* (2018.01); *Y02A 50/491* (2018.01)

(58) Field of Classification Search
CPC ..................................................... C12N 15/85
See application file for complete search history.

(56) References Cited

U.S. PATENT DOCUMENTS

| | | |
|---|---|---|
| 4,642,284 A | 2/1987 | Cooper et al. |
| 5,653,985 A * | 8/1997 | Haigwood ........... C07K 14/005 424/204.1 |
| 6,149,906 A | 11/2000 | Mosca |
| 7,767,202 B2 | 8/2010 | Pardoll et al. |
| 2005/0208029 A1 | 9/2005 | Umezawa et al. |
| 2008/0095750 A1 | 4/2008 | Gimble et al. |
| 2009/0280123 A1 | 11/2009 | Benayahu |
| 2011/0150845 A1 | 6/2011 | Parekkadan et al. |
| 2011/0229499 A1 | 9/2011 | Childs et al. |

FOREIGN PATENT DOCUMENTS

| | | |
|---|---|---|
| WO | 2009129616 A1 | 10/2009 |
| WO | 2010119039 A1 | 10/2010 |

OTHER PUBLICATIONS

Le Blanc et al., 2007, J. Intern. Med., vol. 262, pp. 509-525.*
Thyagarajan et al. (2009, Regen. Med., vol. 4(2), pp. 240-250).*
Tonnchuck et al. (e-Pub Nov. 16, 2012, Front Cell Infect Microbiol., vol. 2(140), pp. 1-8). (Year: 2012).*
Abraham, E.J. et al., Human Pancreatic Islet-Derived Progenitor Cell Engraftment in Immunocompetent Mice, American Journal of Pathology 164 (3), 817-830 (2004).
Aggarwal, S. et al., Human Mesenchymal Stem Cells Modulate Allogenic Immune Cell Responses, Blood 105 (4), 1815-1822 (2005).
Bergfeld, S.A. et al., Bone Marrow-Derived Mesenchymal Stem Cells and the Tumor Microenvironment, Cancer Metastasis Rev. 29, 249-261 (2010).
Bhargava, A., et al., Dendritic Cell Engineering for Tumor Immunotherapy: from Biology to Clinical Translation, Immunotherapy 4 (7), 703-718 (2012).
Bunnell, B.A., et al., New Cconcepts on the Immune Modulation Mediated by Mesenchymal Stem Cells. Stem Cell Research and Therapy 1 (34) 1-8 (2010).
Cavenaugh, J.S. et al., Partially Randomized, Non-Blinded Trial of DNA and MVA Therapeutic Vaccines Based on Hepatitis B Virus Surface Protein for Chronic HBV infection. PloS One 6 (2), e14626, 1-14 (2011).

(Continued)

*Primary Examiner* — Thaian N Ton
*Assistant Examiner* — David A. Montanari
(74) *Attorney, Agent, or Firm* — Olson & Cepuritis, Ltd.

(57) ABSTRACT

Episomally transfected primary mesenchymal stem cells (MSC) express a polypeptide consisting of an antigenic polypeptide (e.g., one or more polypeptides) relating to a pathogen (e.g., one or more virus, bacterium, or parasite). The antigenic polypeptide can have the amino acid sequence of a natural polypeptide from the pathogen or an amino acid sequence differing from the natural sequence by one or more conservative amino acid substitutions. Uses and method for treating or preventing infections with episomally transfected primary MSC also are described.

9 Claims, 5 Drawing Sheets
Specification includes a Sequence Listing.

(56) References Cited

OTHER PUBLICATIONS

Chan, J.L., et al., Antigen-Presenting Property of Mesenchymal Stem Cells Occurs During a Narrow Window at Low Levels of Interferon-Gamma, Blood 107 (12), 4817-4824 (2006).
Chen, B. et al., Flk-1+ Mesenchymal Stem Cells Aggravate Collagen-Induced Arthritis by Up-Regulating Interleukin-6, Clinical and Experimental Immunolgy 159, 292-302 (2009).
Chen, K., et al., Human Umbilical Cord Mesenchymal Stem Cells hUC-MSCs Exert Immunosuppressive Activities Through a PGE2-Dependent Mechanism, Clinical immunology 135, 448-458 (2010).
Chen, X. et al., Mesenchymal Stem Cells in Immunoregulation. Immunology and Cell Biology 84, 413-421 (2006).
Choi, J.J., et al., Mesenchymal Stem Cells Overexpressing Interleukin-10 Attenuate Collagen-Induced Arthritis in Mice, Clinical and Experimental Immunology 153, 269-276 (2008).
Corcione, A., Human Mesenchymal Stem Cells Modulate B-Cell Functions. Blood 107 (1), 367-372 (2006).
Di Nicola, M. et al., Human Bone Marrow Stromal Cells Suppress T-lymphocyte Proliferation Induced by Cellular or Nonspecific Mitogenic Stimuli, Blood 99 (10), 3838-3843 (2002).
Djouad, F. et al., Reversal of the Immunosuppressive Properties of Mesenchymal Stem Cells by Tumor Necrosis Factor Alpha in Collagen-Induced Arthritis, Arthritis & Rheumatism 52 (5), 1595-1603 (2005).
Francois, M. et al., Mesenchymal Stromal Cells Cross-Present Soluble Exogenous Antigens as Part of Their Antigen-Presenting Cell Properties. Blood 24, (114) (13), 2632-2638 (2009).
Franquesa, M.et al., The Impact of Mesenchymal Stem Cell Therapy in Transplant Rejection and Tolerance. Current Opinion in Organ Transplantation 17 (4), 355-361 (2012).
Gao, J.et al., The Dynamic In Vivo Distribution of Bone Marrow-Derived Mesenchymal Stem Cells After Infusion, Cells Tissues Organs 169, 12-20 (2001).
Gotherstrom, C., Immunomodulation by Multipotent Mesenchymal Stromal Cells, Transplantation 84 (1S), S35-37 (2007).
Hung, S-C. et al., Immortalization Without Neoplastic Transformation of Human Mesenchymal Stem Cells by Transduction with HPV16 E6/E7 Genes, International Journal of Cancer 110, 313-319 (2004).
Jankovic, D. et al., Adsorption to Aluminum Hydroxide Promotes the Activity of IL-12 as an Adjuvant for Antibody as Well as Type 1 Cytokine Responses to HIV-1 gp120, The Journal of Immunology 159, 2409-2417 (1997).
Klinge, P.M. et al., Encapsulated Native and Glucagon-Like Peptide-1 Transfected Human Mesenchymal Stem Cells in a Transgenic Mouse Model of Alzheimer's Disease, . Neuroscience Letters 497, 6-10 (2011).
Klopp, A.H. et al., Tumor Irradiation Increases the Recruitment of Circulating Mesenchymal Stem Cells into the Tumor Microenvironment, Cancer Res 67 (24), 11687-11695 (2007).
Kumar, S. et al., Therapeutic Potential of Genetically Modified Adult Stem Cells for Osteopenia, Gene Therapy 17, 105-116 (2010).
Lamalle-Bernard, D. et al., Coadsorption of HIV-1 p24 and gp120 Proteins to Surfactant-Free Anionic PLA Nanoparticles Preserves Antigenicity and Immunogenicity, Journal of Controlled Release 115, 57-67 (2006).
Lamarca, H.L. et al., Epidermal Growth Factor-Stimulated Extravillous Cytotrophoblast Motility is Mediated by the Activation of PI3-K, Akt and Both p38 and p42/44 Mitogen-Activated Protein Kinases, Human Reproduction 23 (8), 1733-1741 (2008).
Le Blanc, K. et al., Multipotent Mesenchymal Stromal Cells and the Innate Immune System, Nature Reviews. Immunology 12, 383-396 (2012).
Le Blanc, K. et al., Immunomodulation by Mesenchymal Stem Cells and Clinical Experience., Journal of Internal Medicine 262, 509-525 (2007).

Li, X. et al., In Vtro Effect of Adenovirus-Mediated Human Gamma Interferon Gene Transfer Into Human Mesenchymal Stem Cells for Chronic Myelogenous Leukemia, Hematological Oncology 24, 151-158 (2006).
Liang, J. et al., Mesenchymal Stem Cell Transplantation for Diffuse Alveolar Hemorrhage in SLE, Nature Reviews. Rheumatology 6, 486-489 (2010).
Lim, J.H. et al., Mesenchymal Stromal Cells for Steroid-Refractory Acute Graft-versus-host disease: A Report of Two Cases. International Journal of Hematology 92, 204-207 (2010).
Liu, X.J. et al., Reciprocal Effect of Mesenchymal Stem Cell on Experimental Autoimmune Encephalomyelitis Is Mediated by Transforming Growth Factor-beta and Interleukin-6, Clinical & Experimental Immunology 158, 37-44 (2009).
Loebinger, M.R. et al., Stem Cells as Vectors for Antitumour Therapy, Thorax 65, 362-369 (2010).
Majumdar, M.K. et al., Characterization and Functionality of Cell Surface Molecules on Human Mesenchymal Stem Cells, Journal of Biomedical Science 10, 228-241 (2003).
Martino, G. et al., Stem Cell Transplantation in Multiple Sclerosis: Current Status and Future Prospects, Nature Reviews, Neurology 6, 247-255 (2010).
McCormick, A.L.et al., Immunization With an Interferon-gamma-gp120 Fusion Protein Induces Enhanced Immune Responses to Human Immunodeficiency Virus gp120, The Journal of Infectious Diseases 184, 1423-1430 (2001).
Meisel, R. et al., Human Bone Marrow Stromal Cells Inhibit Allogeneic T-cell Responses by Indoleamine 2,3-Dioxygenase-Mediated Tryptophan Degradation, Blood 103 (12) 4619-4621 (2004).
Newman, R.E. et al., Treatment of Inflammatory Diseases with Mesenchymal Stem Cells, Inflammation & Allergy Drug Targets 8, 110-123 (2009).
Norton, E.B., Characterization of a Mutant *Escherichia coli* Heat-labile Toxin, LT(R192G/L211A), as a Safe and Effective Oral Adjuvant, Clinical and Vaccine Immunolgy 18 (4), 546-551 (2011).
Ohtaki, H. et al., Stem/Progenitor Cells From Bone Marrow Decrease Neuronal Death in Global Ischemia by Modulation of Inflammatory/immune Responses. Proceeding of the National Academy of Sciences of the United States of America 105 (38) 14638-14643 (2008).
Palucka, K. et al., Cancer Immunotherapy Via Dendritic Cells, Nature Reviews: Cancer 12, 265-277 (2012).
Panes, J. et al., Stem Cell Treatment for Crohn's Disease. Expert Review of Clinical Immunology 6 (4), 597-605 (2010).
Phinney, D.G. et al., Concise Review: Mesenchymal Stem/Multipotent Stromal Cells: The State of Transdifferentiation and Modes of Tissue Repair—Current Views, Stem Cells 25, 2896-2902 (2007).
Potian, J.A. et al., Veto-Like Activity of Mesenchymal Stem Cells: Functional Discrimination Between Cellular Responses to Alloantigens and Recall Antigens, Journal of Immunology 171, 3426-3434 (2003).
Prockop, D.J., Repair of Tissues by Adult Stem/Progenitor Cells (MSCs): Controversies, Myths, and Changing Paradigms, Molecular Therapy 17 (6), 939-946 (2009).
Raffaghello, L. et al., Human Mesenchymal Stem Cells Inhibit Neutrophil Apoptosis: A Model for Neutrophil Preservation in the Bone Marrow Niche, Stem Cells 26, 151-162 (2008).
Rasmusson, I. et al., Mesenchymal Stem Cells Stimulate Antibody Secretion in Human B Cells, Scandinavian Journal of Immunology 65, 336-343 (2007).
Ren, C.et al., Therapeutic Potential of Mesenchymal Stem Cells Producing Interferon-Alpha in a Mouse Melanoma Lung Metastasis Model. Stem Cells 26, 2332-2338 (2008).
Ringden, O. et al., Mesenchymal Stem Cells for Treatment of Therapy-Resistant Graft-Versus-Host Disease, Transplantation 81 (10) 1390-1397 (2006).
Ripoll, C.B. et al., Comparative Characterization of Mesenchymal Stem Cells From eGFP Transgenic and Non-Transgenic Mice, BMC Cell Biology 10 (3), 1-12 (2009).
Rubio, D. et al., Spontaneous Human Adult Stem Cell Transformation, Cancer Research 65, 3035-3039 (2005).

(56) References Cited

OTHER PUBLICATIONS

Abdi, R. et al., Immunomodulation by Mesenchymal Stem Cells, A Potential Therapeutic Strategy for Type 1 Diabetes, Diabetes 57, 1759-1767 (2008).

Balyasnikova, I.V. et al., Genetic Modification of Mesenchymal Stem Cells to Express a Single-Chain Antibody Against EGFRvlll on the Cell Surface, J Tissue Eng Regen Med. 4 (4), 247-258 (2010).

Balyasnikova, I.V. et al., Mesenchymal Stem Cells Modified With a Single-Chain Antibody Against EGFRvlll Successfully Inhibit the Growth of Human Xenograft Malignant Glioma, PLoS One 5 (3) e9750, 1-11 (2010).

Bode, J. et al., The Hitchhiking Principle: Optimizing Episomal Vectors for the Use in Gene Therapy and Biotechnology, Gene Therapy and Molecular Biology 6, 33-46 (2001).

Compte, M et al., Tumor Immunotherapy Using Gene-Modified Human Mesenchymal Stem Cells Loaded Into Synthetic Extracellular Matrix Scaffolds, Stem Cells 27, 753-760 (2009).

Dave, S. D. et al., Ex Vivo Generation of Glucose Sensitive Insulin Secreting Mesenchymal Stem Cells Derived From Human Adipose Tissue, Indian Journal of Endocrinology and Metabolism 16 (1), S65-S69 (2012).

Docheva, D. et al., Mesenchymal Stem Cells and Their Cell Surface Receptors, Current Rheumatology Reviews 4, 1-6 (2008).

Kim, J. H. et al., Generation of Insulin-Producing Human Mesenchymal Stem Cells Using Recombinant Adeno-Associated Virus, Yonsei Medical Journal 48 (1), 109-119 (2007).

Prabakar, K. R. et al., Generation of Glucose-Responsive, Insulin-Producing Cells From Human Umbilical Cord Blood-Derived Mesenchymal Stem Cells, Cell Transplantation 21, 1321-1339 (2012).

Sasaki, M. et al., BDNF-Hypersecreting Human Mesenchymal Stem Cells Promote Functional Recovery, Axonal Sprouting, and Protection of Corticospinal Neurons After Spinal Cord Injury, Journal of Neuroscience 29 (47), 14932-14941 (2009).

Schena, F. et al., Interferon-gamma-Dependent Inhibition of B Cell Activation by Bone Marrow-Derived Mesenchymal Stem Cells in a Murine Model of Systemic Lupus Erythematosus, Arthritis and Rheumatism 62 (9), 2776-2786 (2010).

Song, Y.S. et al., Mesenchymal stem cells over-expressing hepatocyte growth factor (HGF) inhibit collagen deposit and improve bladder function in rat model of bladder outlet obstruction. Cell Transplantation, (2012).

Sotiropoulou, P.A. et al., Interactions Between Human Mesenchymal Stem Cells and Natural Killer Cells. Stem Cells 24, 74-85 (2006).

Spaeth, E. et al., Inflammation and Tumor Microenvironments: Defining the Migratory Itinerary of Mesenchymal Stem Cells, Gene Therapy 15, 730-738 (2008).

Stagg, J. et al., Immune Regulation by Mesenchymal Stem Cells: Two Sides to the Coin, Tissue Antigens: Journal Compilation 69, 1-9 (2006).

Sundin, M. et al., No Alloantibodies Against Mesenchymal Stromal Cells, but Presence of Anti-Fetal Calf Serum Antibodies, After Transplantation in Allogeneic Hematopoietic Stem Cell Recipients, Haematologica/The Hematology Journal 92 (09),1208-1215 (2007).

Tolar, J. et al., Sarcoma Derived From Cultured Mesenchymal Stem Cells, Stem Cells 25, 371-379 (2007).

Tomchuck, S.L. et al., Toll-Like Receptors on Human Mesenchymal Stem Cells Drive Their Migration and Immunomodulating Responses, Stem Cells 26, 99-107 (2008).

Traggiai, E. et al., Bone Marrow-Derived Mesenchymal Stem Cells Induce Both Polyclonal Expansion and Differentiation of B Cells Isolated From Healthy Donors and Systemic Lupus Erythematosus Patients, Stem Cells 26, 562-569 (2008).

Tso, G.H. et al., Phagocytosis of Apoptotic Cells Modulates Mesenchymal Stem Cells Osteogenic Differentiation to Enhance IL-17 and RANKL Expression on CD4+ T Cells, Stem Cells 28, 939-954 (2010).

Uccelli, A. et al., Mesenchymal Stem Cells in Health and Disease, Nature Reviews: Immunology 8, 726-736 (2008).

Uccelli, A. et al., Mesenchymal Stem Cells: A New Strategy for Immunosuppression? Trends in Immunology 28 (5), 219-226 (2007).

Wang, Y. et al., Human Serum Amyloid P Functions as a Negative Regulator of the Innate and Adaptive Immune Responses to DNA Vaccines, Journal of Immunology 186, 2860-2870 (2011).

Waterman, R.S. et al., A New Mesenchymal Stem Cell (MSC) Paradigm: Polarization Into a Pro-Inflammatory MSC1 or an Immunosuppressive MSC2 Phenotype, PloS One 5 (4), e10088: 1-14 (2010).

Wei, H.J. et al., The Development of a Novel Cancer Immunotherapeutic Platform Using Tumor-Targeting Mesenchymal Stem Cells and a Protein Vaccine, Molecular Therapy, 1-9 (2011).

Wernicke, C.M. et al., Mesenchymal Stromal Cells for Treatment of Steroid-Refractory GvHD: A Review of the Literature and Two Pediatric Cases, International Aarchives of Medicine 4 (27), 1-9 (2011).

Yi, T. et al., Immunomodulatory Properties of Mesenchymal Stem Cells and Their Therapeutic Applications, Archives of Pharmacal Research 35 (2), 213-221 (2012).

Suzanne L. Tomchuck et al. "Mesenchymal stem cells as a novel vaccine platform", Frontiers in Cellular and Infection Microbiology, vol. 2, Article 140, pp. 1-8; Nov. 12, 2012.

* cited by examiner

SEQ ID NO: 1:

```
              10         20         30         40         50         60
     MGARASVLSG GKLDKWEKIR LRPGGKKKYR LKHIVWASRE LERFAVNPGL LESSEGCRQI 70         80         90        100        110        120
     LGQLLPALKT GSEELRSLYN TVATLYCVHQ RIEVKDTKEA LEKIEEEQAK SKKKEAAADT 130        140        150        160        170        180
     GNSSQVSQNY PIVQNMQGQM VHQAISPRTL NAWVKVVEEK AFSPEVIPMF SALSEGATPQ 190        200        210        220        230        240
     DLNTMLNTVG GHQAAMQMLK ETINEEAAEW DRLHPVHAGP IAPGQMREPR GSDIAGTTST 250        260        270        280        290        300
     LQEQIGWMTN NPPIPVGEIY KRWIILGLNK IVRMYSPTSI LDIRQGPKEP FRDYVDRFYK 310        320        330        340        350        360
     TLRAEQASQE VKNWMTETLL VQNANPDCKT ILKALGPAAT LEEMMTACQG VGGPGHKARV 370        380        390        400        410        420
     LAEAMSQVTN PATIMMQRGN FRNQRKIVKC FNCGKEGHIA RNCRAPRKKG CWKCGKEGHQ 430        440        450        460        470        480
     MKDCTERQAN FLGKIWPSYK GRPGNFLQSR PEPTAPPEKS FRFGEETATP SQKQEPIDKE

490
     MYPLTSLRSL FGNDPSSQ
```

FIG. 5

PRIMARY MESENCHYMAL STEM CELLS AS A VACCINE PLATFORM

CROSS-REFERENCE TO RELATED APPLICATIONS

This application claims the benefit of U.S. Provisional Application Ser. No. 61/773,546, filed on Mar. 6, 2013, and U.S. Provisional Application Ser. No. 61/745,156, filed on Dec. 21, 2012, each of which is incorporated herein by reference in its entirety.

SEQUENCE LISTING INCORPORATION

Biological sequence information for this application is included in an ASCII text file having the file name "TU-486-2-SEQ.txt", created on Nov. 7, 2013, and having a file size of 4,909 bytes, which is incorporated herein by reference.

FIELD OF THE INVENTION

This invention relates to vaccines. In particular, this invention relates to vaccines comprising primary mesenchymal stem cells for delivery of an pathogenic antigen.

BACKGROUND

While vaccination programs have clear documented success in controlling many diseases, there has been a failure to generate effective, long-term immunity against certain major pathogens. On the other hand, in carcinogenic situations there is an urgent need to develop therapies that promote the host immune system to target and destroy cancerous tumors and metastases. Mesenchymal stem cells (MSC) are unique multipotent progenitor cells that are presently being exploited as gene therapy vectors for a variety of conditions, including cancer and autoimmune diseases (Klopp et al., 2007; Le Blanc and Ringden, 2007; Spaeth et al., 2008; Bergfeld and DeClerck, 2010; Chen et al., 2010; Liang et al., 2010; Martino et al., 2010; Panes et al., 2010). Although MSC are predominantly known for anti-inflammatory properties during allogeneic MSC transplant, there is evidence that MSC can actually promote adaptive immunity under certain settings. MSC have been identified in a wide variety of tissues, including bone marrow, adipose tissue, placenta, and umbilical cord blood. Adipose tissue is one of the richest known sources of MSC.

MSC have been successfully transplanted into allogeneic hosts in a variety of clinical and pre-clinical settings (Di Nicola et al., 2002; Meisel et al., 2004; Aggarwal and Pittenger, 2005; Chen et al., 2006; Corcione et al., 2006; Sotiropoulou et al., 2006; Uccelli et al., 2007; Raffaghello et al., 2008). These donor MSC often promote immunotolerance (Potian et al., 2003; Aggarwal and Pittenger, 2005), including the inhibition of graft-versus-host disease (GvHD) that can develop after cell or tissue transplantation from a major histocompatibility complex (MHC)-mismatched donor (Ringden et al., 2006; Wernicke et al., 2011). The diminished GvHD symptoms after MSC transfer has been due to direct MSC inhibition of T and B cell proliferation, resting natural killer cell cytotoxicity, and DC maturation (reviewed in (Uccelli et al., 2008)). At least one study has reported generation of antibodies against transplanted allogeneic MSC (Sundin et al., 2007). Nevertheless, the ability to prevent GvHD also suggests that MSC expressing foreign antigen might have an advantage over other cell types (i.e., dendritic cells; DC) during a cellular vaccination in selectively inducing immune responses to only the foreign antigen(s) expressed by MSC and not specifically the donor MSC. Use of MSC as the cellular base for an alternative vaccination strategy may save on production time and costs associated with necessary HLA matching if other cell types were used.

The use of modified MSC also is being explored in vivo in order to enhance the immunomodulatory properties of MSC (Choi et al., 2008; Sasaki et al., 2009; Kumar et al., 2010; Klinge et al., 2011). MSC transduced to overproduce IL-10 suppressed collagen-induced arthritis in a mouse model (Choi et al., 2008). In addition, MSC expressing glucagon-like peptide-1 transplanted into an Alzheimer's disease mouse model led to a decrease in A-beta deposition in the brain (Klinge et al., 2011). In an osteopenia mouse model, mice receiving transduced MSC that had stable expression of bone morphogenetic protein had increased bone density (Kumar et al., 2010). In a rat model for spinal cord injury, rats treated with MSC stably overexpressing of brain-derived neurotrophic factor had a better overall outcome than rats administered MSC alone (Sasaki et al., 2009). Lastly, in a rat model for bladder outlet obstruction, rats receiving transduced MSC with stable overexpression of hepatocyte growth factor had decreased collagen accumulation in the bladder (Song et al., 2012). These studies indicate that modified MSC are a useful and feasible vehicle for protein expression/delivery to target various diseases and tissues.

MSC have been studied as a delivery vehicle for anti-cancer therapeutics due to their innate tendency to home to tumor microenvironments, and is thoroughly reviewed in (Loebinger and Janes, 2010). MSC have also been used to promote apoptosis of tumorigenic cells through the expression of IFNα or IFNγ (Li et al., 2006; Ren et al., 2008). Additionally, MSC have recently been explored for the prevention and inhibition of tumorigenesis and metastasis. A study by Wei et al. examined the use of human papilloma virus (HPV)-immortalized MSC that express the HPV proteins E6/E7 combined with a modified E7 fusion protein vaccine in a mouse tumor model where metastatic fibrosarcoma cells were administered (Wei et al., 2011). This group found that only mice that were immunized with both the E7-expressing MSC and modified E7 protein vaccine showed a decrease in tumor growth, and an E7-specific antibody response. Mice receiving either MSC or protein vaccine alone were not able to raise an anti-E7 response or inhibit tumor growth of metastatic sarcoma. The limitation of this interesting approach is that it can only be used as an anti-cancer therapeutic and not as a universal cancer preventative, as individual tumors have unique antigen expression. In addition, a long-term safety examination of these immortalized MSC/protein vaccine therapy in cancer-free mice is warranted. Although these immortalized MSC were previously determined to be non-tumorigenic (Hung et al., 2004), they persisted in mice longer than 21 days, unlike primary MSC (i.e. non-immortalized), which are only detectable for a very short time after administration (Gao et al., 2001; Abraham et al., 2004; Ohtaki et al., 2008; Prockop, 2009). Thus, there may be unforeseen outcomes in the long term (i.e. outcompeting with endogenous MSC and differing immunomodulatory abilities, which were not assessed in this study) with the use of immortalized MSC even if they prove to be non-malignant. Other studies have indicated that immortalized MSC can become tumorigenic, and thus must be carefully studied to determine if they are indeed safe for use (Rubio et al., 2005; Phinney and Prockop, 2007; Tolar et al., 2007).

Vaccines generally are considered to be one of the most efficient and cost-effective means of preventing infectious disease. Vaccines have already demonstrated transformative potential in eradicating one devastating disease, smallpox, while offering the ability to control other diseases, including diphtheria, polio, and measles, that formerly caused widespread morbidity and mortality. The development of vaccines involves the testing of an attenuated or inactivated version of the pathogen or identification of a pathogen component(s) (i.e. subunit, toxoid, virus-like particle) that elicits an immune response that protects recipients from disease when they are exposed to the actual pathogen. In an ideal world a single vaccine would be able to target all major human pathogens (versatile), elicit strong protective immunity to these pathogens (robust) without inducing unwanted side-effects (safe), and still be fairly inexpensive to produce per dose (cost-effective). In the case of viruses or host-cell produced proteins, vaccine production that includes human post-translational processing, mimicking natural infection, will likely prove to be superior to bacterial or other expression systems.

Traditional vaccine approaches have thus far failed to provide protection against HIV, tuberculosis, malaria and many other diseases, including dengue, herpes and even the common cold. The reasons why traditional vaccine approaches have not been successful for these diseases are complex and varied. For example, HIV integrates functional proviral genomes into the DNA of host cells, thereby establishing latency or persistence. Once latency/persistence is established, it has not been possible to eradicate HIV, even with highly active antiretroviral therapy. Clearly, new approaches to vaccine development are needed to address HIV and other intractable vaccine challenges.

Newer alternative immunization approaches include both DNA and cellular vaccines. DNA vaccines involve the transfection of cells at the tissue site of vaccination with an antigen-encoding plasmid that allows local cells (i.e. myocytes) to produce the vaccine antigen in situ. Cellular vaccines use the direct transfer of pre-pulsed or transfected host cells (i.e. dendritic cells, DC) expressing or presenting the vaccine antigen. The advantage of these approaches is that vaccine antigens are produced in vivo and are readily available for immunological processing. Despite numerous reports of successful pre-clinical testing, both such approaches have hit stumbling blocks. DNA vaccination studies in humans show poor efficacy, which was linked to innate differences between mice and humans (Cavenaugh et al., 2011; Wang et al., 2011). DC vaccination strategies have shown limited clinical success for therapeutic cancer vaccinations and have high production costs due to necessary individual tailoring (Bhargava et al., 2012; Palucka and Banchereau, 2012).

There is an ongoing need for new strategies for vaccination against infectious diseases. The episomally transfected MSC and methods described herein address these needs.

SUMMARY OF THE INVENTION

Episomally transfected primary mesenchymal stems cells (ETP-MSC) that express (i.e., episomally express) at least one polypeptide (e.g., one or more polypeptides) consisting of an antigenic polypeptide relating to a pathogen (e.g., one or more pathogen) are described herein.

In some embodiments the ETP-MSC express a plurality (e.g., 2 to about 10, 20, 50, 100, 200, or 500) of antigenic polypeptides from a pathogen (e.g., an infectious species of virus, bacterium, or parasite). For example, the antigenic polypeptide can be a protein or fragment thereof from a pathogenic organism or can be otherwise related to a pathogenic organism, e.g., by conservative substitutions in the amino acid sequence of a protein or protein fragment from the pathogen. The ETP-MSC may be transfected to episomally express antigenic polypeptides from a plurality (e.g., 2 or more) pathogens (e.g., 2 to 10 pathogens), if desired. The ETP-MSC are useful for treating or preventing an infection by the pathogen.

The ETP-MSC can be provided in a pharmaceutically acceptable carrier (e.g., an aqueous carrier such as physiological saline, a buffer such as phosphate buffered saline, and the like, optionally including one or more adjuvant materials such as stem cell nutrients) for use as a pharmaceutical composition or vaccine for respectively treating or preventing an infectious disease caused by the pathogen.

In a preferred embodiment, the ETP-MSC do not express an immune regulatory of costimulatory molecule. In some embodiments, the ETP-MSC comprise bone marrow-derived cells, while in some other embodiments, the ETP-MSC comprise adipose-derived MSC cells, placental-derived MSC cells, peripheral blood-derived MSC, or umbilical cord-derived MSC cells (e.g., from Wharton's jelly).

A method for treating or preventing an infection caused by a pathogenic species also is described. The method comprises administering to a subject a therapeutic or prophylactic dosage of the episomally transfected primary MCS as described herein.

The ETP-MSC described herein are particularly useful for vaccination against pathogens, at least in part, because primary MSC are hypo-immunogenic cells that generally are not targeted by the immune system. Thus, the ETP-MSC are tolerated by the patient, allowing the cells to survive for a sufficient time for antigenic polypeptide to be expressed for presentation by antigen-presenting cells (APC). In addition, the use of primary MSC sources instead of immortalized MSC is preferred for this vaccine approach. In certain studies, immortalized MSC were previously determined to be non-tumorigenic (Hung et al., 2004) as described by Wei et al.; however, immortalized MSC persisted in mice longer than 21 days, unlike primary MSC (i.e. non-immortalized), which are only detectable for a very short time after administration (Gao et al., 2001; Abraham et al., 2004; Ohtaki et al., 2008; Prockop, 2009). Thus, there may be unforeseen outcomes in the long term (i.e. outcompeting with endogenous MSC and differing immunomodulatory abilities, which were not assessed in this study) with the use of immortalized MSC even if they prove to be non-malignant. Other studies have indicated that immortalized MSC can become tumorigenic, and thus must be carefully studied to determine if they are indeed safe for use (Rubio et al., 2005; Phinney and Prockop, 2007; Tolar et al., 2007). Furthermore, in terms of a vaccine approach, a chronic exposure of the patient to immortalized MSC expressing antigenic polypeptides instead of a transient exposure to the antigen using primary MSC may not yield the most efficient protective effect to the corresponding pathogen and may cause unwanted side effects.

BRIEF DESCRIPTION OF THE DRAWINGS

FIG. 5 provides the amino acid sequence of gp120 (SEQ ID NO: 1).

DETAILED DESCRIPTION OF PREFERRED EMBODIMENTS

Figure 1:
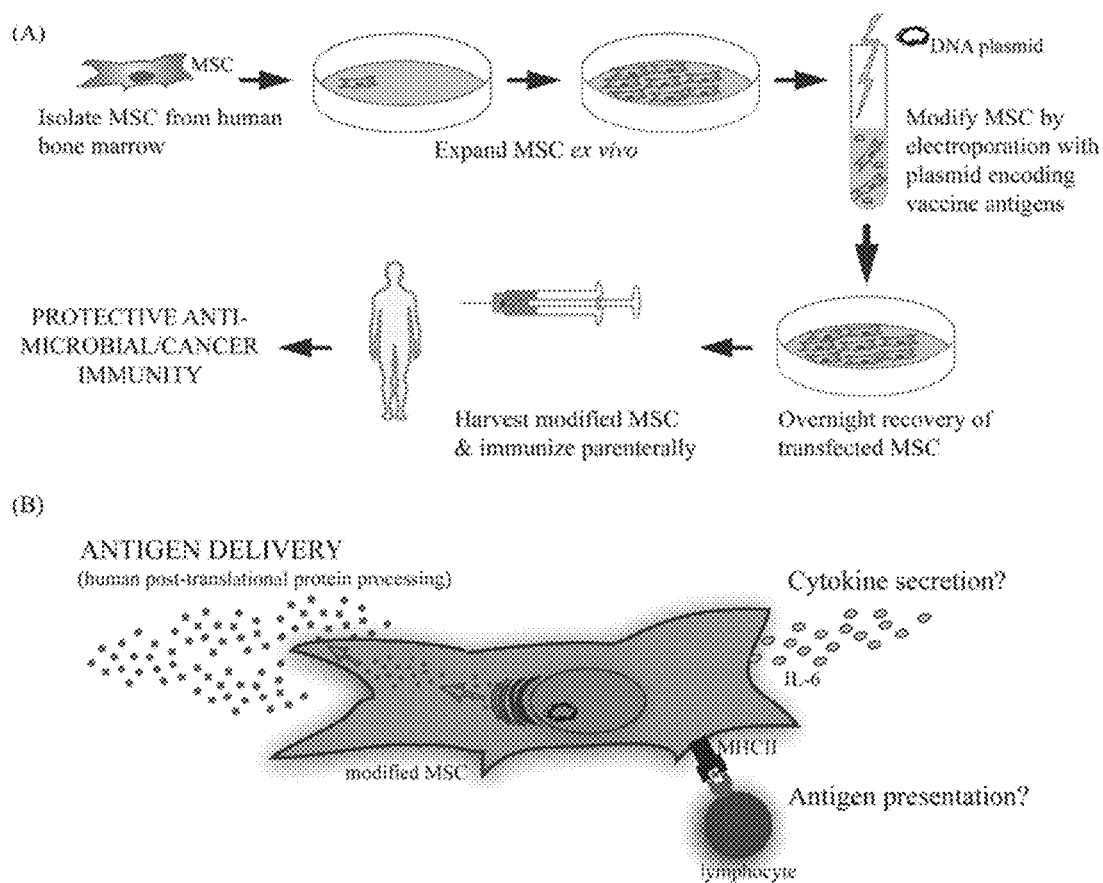
FIG. 1 provides a schematic representation of a method for vaccination with episomally transfected primary MSC as described; (A) illustrates expansion and episomal transfection of primary MSC isolated from the bone marrow of human donors; (B) schematically illustrates functions of the transfected ETP-MSC after vaccination.

Episomally transfected primary mesenchymal stem cells described herein express at least one polypeptide consisting of an antigenic polypeptide relating to a pathogen, such as a viral, bacterial or parasitic species (e.g., a single celled parasite or a multicellular parasite) are described herein. The primary MSC are transfected episomally so that genome of the MSC is not modified, and the cells appear to the immune system of a subject treated with the MSC as substantially normal primary MSC. In some embodiments, the ETP-MSC are transfected to express a plurality of the antigenic polypeptides. In other embodiments, the ETP-MSC are transfected to episomally express antigenic polypeptides from a plurality of pathogens. Uses and method for treating an ongoing infection (e.g., as a therapeutic pharmaceutical composition or therapeutic vaccine) or preventing an infection (e.g., as a prophylactic vaccine) with the ETP-MSC also are described. In some embodiments, the MSC also are episomally transfected to express other polypeptides in addition to the pathogen polypeptide, e.g., a costimulatory molecule such as B7.1 or B7.2.

Non-limiting examples of viral pathogens from which the antigenic polypeptide or polypeptides can be derived include: adenoviruses; papillomaviruses; hepadnaviruses (e.g., hepatitis B); parvoviruses; pox viruses (e.g., small pox virus, vaccinia virus); Epstein-Barr virus; cytomegalovirus (CMV); herpes simplex viruses; roseolovirus; varicella zoster virus; filoviruses (e.g., Ebola virus and Marburg virus); paramyxoviruses (e.g., measles virus, mumps virus, Nipah virus, Hendra virus, human respiratory syncytial virus (RSV), parainfluenza viruses, Newcastle disease virus, and human metapneumovirus); orthomyxoviruses (e.g., influenza A, influenza B, and influenza C); rhabdoviruses (e.g., Lyssavirus, also known as rabies virus); arenaviruses (e.g., Lassa virus); coronaviruses (severe acute respiratory syndrome (SARS)); human enteroviruses; hepatitis A virus; human rhinoviruses; polio virus; retroviruses (e.g., human immunodeficiency virus 1 (HIV-1)); rotaviruses; flaviviruses, (e.g., West Nile virus, dengue virus, yellow fever virus); hepaciviruses (e.g., hepatitis C virus); and rubella virus.

Non-limiting examples of bacterial pathogens from which the antigenic polypeptide or polypeptides can be derived include any pathogenic bacterial species from a genus selected from: *Bacillus; Bordetella; Borrelia; Brucella; Burkholderia; Campylobacter; Chlamydia, Chlamydophila; Clostridium; Corynebacterium; Enterococcus; Escherichia; Francisella; Haemophilus; Helicobacter; Legionella; Leptospira; Listeria; Mycobacterium; Mycoplasma; Neisseria; Pseudomonas; Rickettsia; Salmonella; Shigella; Staphylococcus; Streptococcus; Treponema; Vibrio*; and *Yersinia*.

Non-limiting examples of parasitic pathogens from which the antigenic polypeptide or polypeptides can be derived include single cell and multicellular parasites, such as: *Acanthamoeba; Anisakis; Ascaris lumbricoides; Balantidium coli; Cestoda* (tapeworm); Chiggers; *Cochliomyia hominivorax; Entamoeba histolytica; Fasciola hepatica; Giardia lamblia*; Hookworm; *Leishmania; Linguatula serrata*; Liver fluke; Loa loa; *Paragonimus* (lung fluke); Pinworm; *Plasmodium falciparum; Schistosoma; Strongyloides stercoralis*, Tapeworm, *Toxoplasma gondii; Trypanosoma*; Whipworm; and *Wuchereria bancrofti*.

Non-limiting examples of viral antigenic polypeptides include: influenza polypeptides such as hemagglutinin 1 (HA1), hemagglutinin 2 (HA2), and neuraminidase (NA); Lassa virus (LASV) polypeptides such as LASV glycoprotein 1 (gp1), LASV glycoprotein 2 (gp2), LASV nucleocapsid-associated protein (NP), LASV L protein, and LASV Z protein; SARS virus polypeptides such as SARS virus S protein; Ebola virus polypeptides such as Ebola virus GP2; measles virus polypeptides such as measles virus fusion 1 (F1) protein; HIV-1 polypeptides such as HIV transmembrane (TM) protein, HIV glycoprotein 41 (gp41), HIV glycoprotein 120 (gp120); hepatitis C virus (HCV) polypeptides such as HCV envelope glycoprotein 1 (E1), HCV envelope glycoprotein 2 (E2), HCV nucleocapsid protein (p22); West Nile virus (WNV) polypeptides such as WNV envelope glycoprotein (E); Japanese encephalitis virus (JEV) polypeptides such as JEV envelope glycoprotein (E); yellow fever virus (YFV) polypeptides such as YFV envelope glycoprotein (E); tick-borne encephalitis virus (TBEV) polypeptides such as TBEV envelope glycoprotein (E); hepatitis G virus (HGV) polypeptides such as HGV envelope glycoprotein 1 (E1); respiratory synctival virus (RSV) polypeptides such as RSV fusion (F) protein; herpes simplex virus (HSV) polypeptides such as HSV-1 gD protein, HSV-1 gG protein, HSV-2 gD protein, and HSV-2 gG protein; hepatitis B virus (HBV) polypeptides such as HBV core protein; and Epstein-Barr virus (EBV) polypeptides such as EBV glycoprotein 125 (gp125).

Non-limiting examples of bacterial antigenic polypeptides include: outer membrane protein assembly factor BamA; translocation assembly module protein TamA; polypeptide-transport associated protein domain protein; bacterial surface antigen D15 from a wide variety of bacterial species; *Bacillus anthracis* polypeptides such as anthrax protective protein, anthrax lethal factor, and anthrax edema factor; *Salmonella typhii* polypeptides such as S1Da and S1Db; *Vibrio cholerae* polypeptides such as cholera toxin and cholera heat shock protein; *Clostridium botulinum* polypeptides such as antigen S and botulinum toxin; and *Yersina pestis* polypeptides such as F1, V antigen, YopH, YopM, YopD, and plasminogen activation factor (Pla).

Non-limiting examples of parasite antigenic polypeptides include: malarial (Plasmodium) polypeptides such as circumsporozoite protein (CSP), sporozoite surface protein (SSP2/TRAP), liver stage antigen 1 (LSAT), exported protein 1 (EXP 1), erythrocyte binding antigen 175 (EBA-175), cysteine-rich protective antigen (cyRPA), and *Plasmodium* heat shock protein 70 (hsp70); and *Schistosoma* polypeptides such as Sm29 and signal transduction protein 14-3-3.

As used herein, the phrase "antigenic polypeptide relating to a pathogen" and grammatical variations thereof, refers to a native protein or fragment thereof from a pathogenic organism, which can elicit an immune response by virtue of one or more epitope sequence present on the polypeptide, as well as polypeptides that include conservative substitutions in the structure of a native antigen from a pathogenic organism. Preferably, polypeptides that differ from a native antigenic polypeptide by one or more conservative substitutions share at least about 50% sequence identity with the natural antigen (e.g., at least about 55, 60, 65, 70, 75, 80, 85, 90, 95 or 98% sequence identity with the native antigen sequence). The ETP-MSC may serve as delivery vehicles or depots for the antigenic polypeptides after vaccination with the ETP-MSC. In addition, the MSC may take a more active role in induction of adaptive immunity such as cytokine excretion (e.g., IL-6), antigen presentation by phagocytosis, or antigen display in a major histocompatibility complex (MHC) molecule, such as a MHC class II molecule (see e.g., FIG. 1, Panel B).

Preferably, the MSC are administered parenterally (e.g. intravenous, subcutaneous, or intramuscular injection or infusion). The isolated MSC can be formulated as a solution, suspension, or emulsion in association with a pharmaceutically acceptable carrier vehicle (e.g., sterile water, saline, dextrose solution, phosphate buffered saline, and the like). Optionally, additives that maintain isotonicity (e.g. mannitol) or chemical stability (e.g. preservatives) can be included in the carrier.

As used herein, a "therapeutically effective dosage" is an amount (e.g., number of ETP-MSC) such that when administered, the ETP-MSC result in a reduction or elimination of already present disease symptoms (e.g., about one hundred thousand to about one hundred million cells). The dosage and number of doses (e.g. single or multiple dose) administered to a subject will vary depending upon a variety of factors, including the route of administration, patient conditions and characteristics (sex, age, body weight, health, size), extent of symptoms, concurrent treatments, frequency of treatment and the effect desired, the identity and number of antigenic polypeptides expressed by the ETP-MSC, and the like. Adjustment and manipulation of established dosage ranges, as well as in vitro and in vivo methods of determining the therapeutic effectiveness of the ETP-MSC in an individual, are well within the ability of those of ordinary skill in the medical arts.

A "prophylactic dosage" is an amount such that when administered, the MSC prevent infection by the pathogen from which the polypeptide expressed by the ETP-MSC was derived (e.g., about one hundred thousand to about one hundred million cells). The dosage and number of doses (e.g. single or multiple dose) administered to a subject will vary depending upon a variety of factors, including the route of administration, patient conditions and characteristics (sex, age, body weight, health, size), extent of symptoms, concurrent treatments, frequency of treatment and the effect desired, the identity and number of antigenic polypeptides expressed by the ETP-MSC, and the like. Adjustment and manipulation of established dosage ranges, as well as in vitro and in vivo methods of determining the prophylactic effectiveness of the ETP-MSC in an individual, are well within the ability of those of ordinary skill in the medical arts.

As used herein, the term "episomally transfected" and grammatical variations thereof refer to non-integrating transfection with exogenous episomal DNA (e.g. a plasmid or other episomal vector) to produce a cell with unaltered chromosomal DNA, in which the a polypeptide encoded by the DNA is expressed in an episome within the MSC, i.e., without genomic integration of the exogenous DNA. As used herein, the term "episome" an grammatical variations thereof refers to closed circular DNA molecules that are replicated in the nucleus, and is intended to encompass exogenous plasmids introduced into the MSC. Preferably, primary MSC are transfected with a plasmid that encodes the antigenic polypeptide, and preferably also encodes regulatory elements (e.g., a promoter) to facilitate episomal expression of the antigenic polypeptide. Optionally, the also MSC can be episomally transfected with a gene to induce cell death (apoptosis) when activated by a suitable signal (e.g., using Tetracycline-Controlled Transcriptional Activation, also referred to as "Tet-on and Tet-off", in which tetracycline or doxycycline is used to turn on transcription of the apoptotic gene), so that the ETP-MSC can be eliminated from the subject if desired or needed (e.g., if undesired side-affects develop). The term "episomal vector" refers to an expression vector comprising plasmid or other circular DNA encoding the antigenic polypeptide.

Primary MSC can be episomally transfected by any suitable methodology. For example, the Primary MSC can be transfected with a plasmid encoding the antigenic polypeptide using electroporation, lipofection, and the like. Electroporation is the preferred method for transfection, unlike other transfection approaches using cationic lipids (i.e. lipofection) as there may be residual lipids after transfection that may not be completely removed when processing the MSC for delivery, and may result in unforeseen side effects.

Non limiting examples of episomal vectors suitable for use as non-integrating vectors for transfection of eukaryotic cells (e.g., primary MSC) include simian virus 40-based vectors, Epstein-Barr virus-based vectors, papilloma virus-based vectors, BK virus-based vectors, and the like, which are well known in the molecular genetics art.

MSC are unique multipotent stromal stem cells present in a number of different tissues (e.g., bone marrow, adipose tissue, and the like), which presently are being exploited as gene therapy vectors for a variety of conditions, including cancer and autoimmune diseases (Klopp et al., 2007; Le Blanc and Ringden, 2007; Spaeth et al., 2008; Bergfeld and DeClerck, 2010; Liang et al., 2010; Lim et al., 2010; Martino et al., 2010; Panes et al., 2010). These cells are known to migrate to sites of inflammation, infection, tissue injury and tumors where they immunomodulate the microenvironment through cell-to-cell contact and the release of soluble factors, thus facilitating the repair of damaged tissue (Aggarwal and Pittenger, 2005; Gotherstrom, 2007). For more information see recent reviews on the immunomodulatory properties of MSC therapy (Le Blanc and Ringden, 2007; Stagg, 2007; Tolar et al., 2007; Franquesa et al., 2012; Yi and Song, 2012).

An important contributing factor to therapeutics designed around MSC is the ease of MSC isolation and expansion in culture. Theoretically, a single bone marrow harvest of MSC may yield sufficient MSC for thousands of clinical applications, due to their inherent expansion capability (Newman et al., 2009). Such expansion potential greatly enhances the GMP manufacturing capability of using MSC for clinical applications and has lower production costs when compared to other cell types.

As described herein, MSC are transfected with one or more antigenic epitopes to a pathogen protein, such as a virus, bacterium or parasite FIG. 1, Panel A, illustrates some unique properties of the modified MSC described herein, which enable these cells to serve as an unconventional but innovative, vaccine platform. Such a platform is capable of expressing hundreds of proteins, thereby generating a broad array of epitopes with correct post-translational processing, mimicking natural infection. The ability of modified MSC to express and secrete a viral antigen that stimulates antigen-specific antibody production in vivo is described herein.

MSC as a vaccine platform. An MSC delivery platform is similar to that of a DNA vaccine or cellular vaccine in that the antigen is expressed through DNA transfection and delivered by an ex vivo cultured cell. The present MSC strategy improves on problems that have occurred with DNA and DC-based vaccinations.

Figure 2:
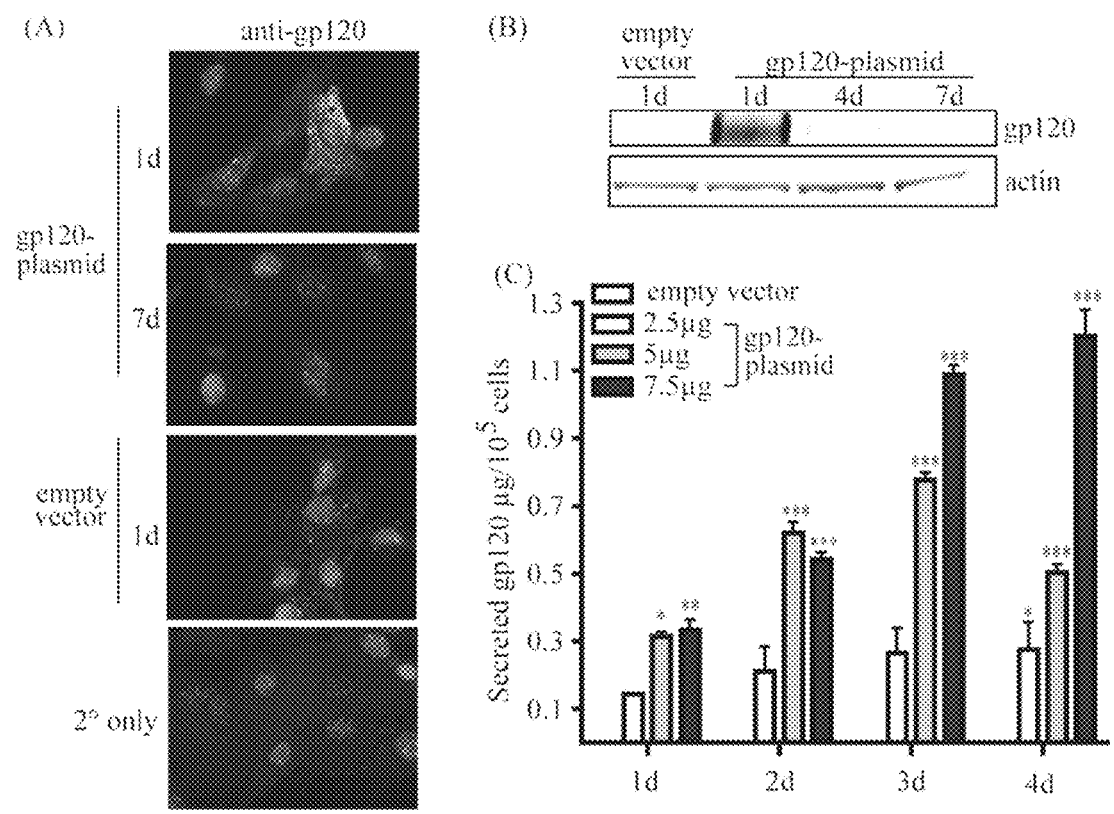
FIG. 2 illustrates that ETP-MSC can be transfected to episomally express viral protein gp120; (A) shows gp120 immunofluorescence staining of episomally transfected primary MSC; (B) shows Western blot analysis of cell lysates; (C) provides HIV-1 gp120 ELISA results.

Anti-microbial prophylactic vaccines. The present invention utilizes primary MSC as a novel platform for a prophylactic vaccine or, in some cases a treatment (a therapeutic vaccine), for infectious disease. MSC that have been modified to express a foreign antigen are sufficient to elicit an antibody-mediated immune response without the need for additional adjuvants or boosting. As described herein, primary MSC can be readily modified to secrete a foreign antigen (e.g., an immunogenic viral, bacterial, or parasite-derived polypeptide) and stimulate antigen-specific antibody production in vivo. For example, MSC were transfected with a plasmid encoding gp120, the glycoprotein from HIV. These transfected MSC transiently express high levels of gp120 protein intracellularly, with the peak expression about one day post-transfection (FIG. 2, Panels A and B). Following transfection, MSC then secreted significant amounts of gp120 protein over one to four days in culture (FIG. 2, Panel C). These expression levels were controllable in a dose-dependent manner based on the amount of plasmid used during the transfection process. For example, by two days post-transfection MSC secreted $2.11\pm0.73$, $6.22\pm2.98$ or $5.41\pm2.25$ μg of gp120 per million cells when transfected with 2.5, 5 or 7.5 μg of vector respectively. Four days post-transfection these cells secreted $2.75\pm0.81$, $5.04\pm0.252$ or $12.03\pm0.77$ μg gp120 respectively. The levels of antigen produced in this transient transfection are sufficient to induce an immunological response from a vaccine standpoint.

Figure 3:
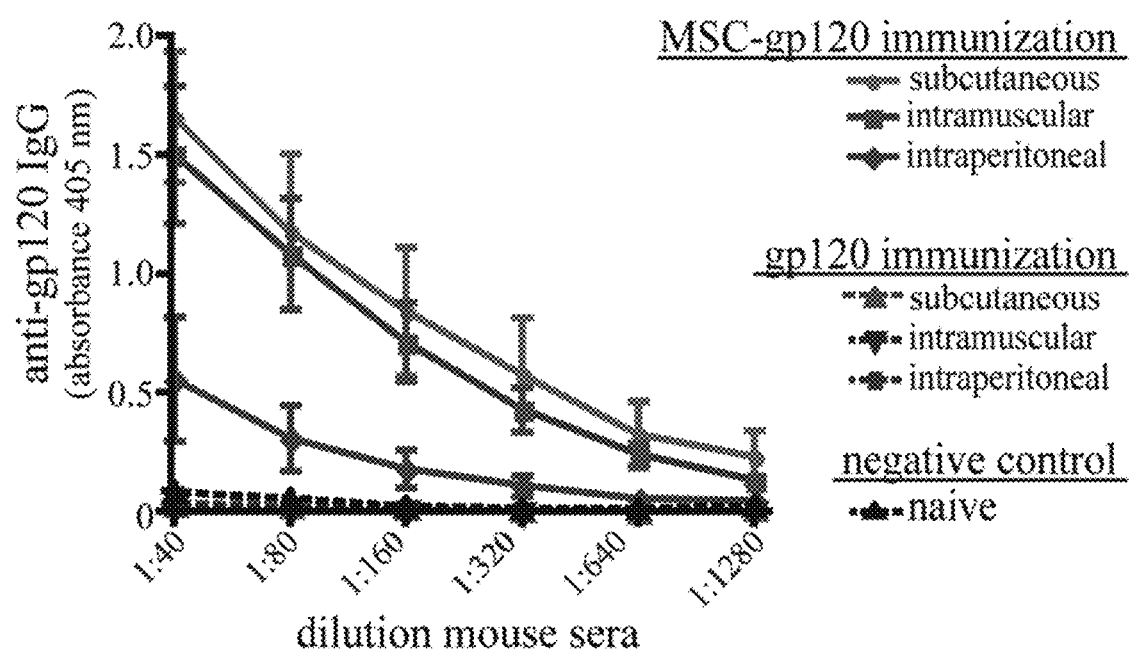
FIG. 3 illustrates ELISA results for serum anti-gp120 IgG antibodies graphed as 405 nm absorbance versus sera dilution.

To examine the ability of transfected MSC to elicit an in vivo antibody response, C57Bl/6 mice were immunized once by intraperitoneal (IP), subcutaneous (SC) or intramuscular (IM) routes using either MSC-gp120 or purified gp120. Since transplanted MSC persist only for a few days at most in vivo (Gao et al., 2001; Abraham et al., 2004; Ohtaki et al., 2008; Prockop, 2009), 5 μg of gp120 was chosen as an amount equivalent to antigen secreted by MSC-gp120, transfected with 7.5 μg of pSWTK-gp120. Similar to other published studies, a single gp120 protein immunization produced no detectable serum antibodies by 17 days post-immunization (Jankovic et al., 1997; McCormick et al., 2001; Lamalle-Bernard et al., 2006) (FIG. 3). Mice immunized with MSC expressing an empty vector also did not elicit serum anti-gp120 responses above sera of naïve mice (data not shown). Surprisingly, all mouse groups receiving an MSC-gp120 immunization developed high-titer serum anti-gp120 IgG antibodies regardless of IP, SC or IM delivery. Thus, delivery of the gp120 antigen was effective at generating an antibody response whereas direct administration of the gp120 protein, per se, was not.

Evidence that MSC can Promote Adaptive Immunity.

The studies described herein with gp120 antigen indicate that modified MSC can deliver antigen for protective vaccination against an infectious disease. However, the exact mechanisms whereby MSC might be directly influencing the generation of immune responses are unknown. The experimental data provided herein suggest a pertinent role for MSC as more than just a delivery vehicle; gp120 alone (at the estimated dose of MSC-gp120 expression) elicited undetectable humoral responses, similar to previous studies (Jankovic et al., 1997; McCormick et al., 2001; Lamalle-Bernard et al., 2006), while MSC-gp120 induced significant anti-gp120 antibodies after a single immunization.

While MSC are primarily touted for their immunosuppressive properties, several published reports have also directly shown that MSC promote adaptive immunity. Table 1 lists publications in which investigators reported MSC-driven activation of T-cells and B-cell responses, mainly through cytokine secretion or antigen-presentation in a variety of experimental settings. In co-cultures, MSC enhanced B-cell proliferation, IL-6 expression and IgG-secreting plasma cell formation in vitro; these B-cell responses could be further augmented with MSC combined with a TLR agonist (lipopolysaccharide or CpG DNA) (Rasmusson et al., 2007; Traggiai et al., 2008). MSC pulsed with tetanus toxoid promoted the proliferation and cytokine expression (IL-4, IL-10, IFNγ) of a tetanus toxoid-specific CD4 T-cell line (Majumdar et al., 2003; Stagg, 2007; Francois et al., 2009). Similarly, MSC cultured in low ratios (1:100) with lymphocytes in the presence of antigen improved lymphocyte proliferation and CD4 Th17 subset formation, which was partially IL-6 and TGFβ-dependent (Liu et al., 2009). MSC have also been found to express MHC-I and cross-present antigen for expansion of CD8 T-cells both in vitro and in vivo (Majumdar et al., 2003; Stagg, 2007; Francois et al., 2009).

MSC immunoregulation has also been found to be dependent upon external signals. In the presence of inflammatory cytokines or stimulants, MSC therapy, which was previously suppressive, can become immunostimulatory. For example, MSC treated with specific pathogen-associated molecular pattern (PAMP) molecules can become either anti- or pro-inflammatory, depending on the PAMP with which they are treated in vitro (Tomchuck et al., 2008; Waterman et al., 2010), reviewed more thoroughly in (Bunnell et al., 2010; Le Blanc and Mougiakakos, 2012). Djouad et al. found that during collagen-induced arthritis, an inflammatory disease setting, transplantation of allogeneic MSC enhanced Th1 immune responses and IL-6 secretion, which was mimicked in vitro by direct TNFα stimulation of MSC (Djouad et al., 2005). A similar study also found MSC administration exacerbated collagen-induced arthritis disease and amplified splenocyte secretion of IL-6 and IL-17 (Chen et al., 2009). Furthermore, pre-treatment of MSC with IFNγ (within a moderate range) upregulates MHC-I and II expression and improves antigen phagocytosis and presentation capabilities, thereby stimulating CD4 and CD8 T-cell proliferation and generation of anti-tumor CD8+ cytotoxic T-lymphocytes (CTLs) (Majumdar et al., 2003; Chan et al., 2006; Stagg, 2007; Francois et al., 2009; Schena et al., 2010). In another study, co-culture of MSC with apoptotic cells, which mimics conditions of rheumatoid arthritis, induced Th17 cells through IL-6 expression on MHC-II expressing MSC (Tso et al., 2010).

These studies further support the methods described herein for use of MSC as a novel vaccination platform generating protective immunity. These studies also suggest mechanisms that may be involved during modified MSCs vaccination besides antigen delivery, including cytokine secretion and antigen presentation (FIG. 1, Panel B). While not always explicitly required, the enhanced promotion of immunity by MSC seen with cytokine or PAMP treatment indicates that vaccine antigens that are highly immunogenic may direct a more immunostimulatory phenotype of the MSC used for vaccination. For example, MSC modified to express a bacterial or viral TLR ligand, in conjunction with other pertinent microbial antigens, may be able to promote even higher levels of protective antigen-specific immunity than microbial antigens by themselves. In addition, the modification process combined with the expression of any antigen may provide some sort of 'inflammatory' signal to the MSC that could positively impact subsequent generation of vaccination responses.

TABLE 1

Evidence that MSC can promote adaptive immunity.
MSC Promotion of Adaptive Immunity

| Experimental Setting | Defined MSC Function | Immunologic Outcome | Reference |
|---|---|---|---|
| In vitro culture of B-cells/splenocytes and MSC +/− TLR agonists (LPS, CpG) | IL-6 secretion | B-cell proliferation IgG secretion | Rasmusson et al., 2007 Traggiai et al., 2008 |
| In vitro culture of antigen-specific CD4 T-cells, MSC, and antigen | MHC-II antigen-presentation IL-6, TGFβ secretion | T-cell proliferation IL-4, IL-10, IFNγ secretion Lymphocyte proliferation Th17 | Majumdar et al., 2003 Liu et al., 2009 |
| In vitro cultures of splenocytes and MSC; Mouse models of collagen-induced arthritis | IL-6 secretion | Th1 Lymphocyte proliferation, IL-6, IL-17 | Djouad et al., 2005 Chen et al., 2009 |
| IFNγ stimulation (moderate levels) during in vitro cultures of T-cells and MSC; Mouse model of systemic lupus erythematosus | MHC-I/II antigen-presentation, phagocytosis | CD4 & CD8 T-cell proliferation, Anti-tumor CD8+ CTLs | Majumdar et al., 2003; Chan et al., 2006; Stagg, 2007; Francois et al., 2009; Schena et al., 2010 |
| In vitro culture with apoptotic cells and CD4 T-cells | MHC-II expression, IL-6 secretion | Th17 cells | Tso et al., 2010 |

It is particularly exciting that MSC may be able to enhance immune responses by direct antigen presentation to T-cells. This possible ability of MSC to act as conditional APCs, but with less risk for GvHD, makes them an attractive alternative to other cellular-based vaccinations. One aspect of transfected MSC for vaccination is the difference in immunologic responses between stable-transfection strategies versus transient-transfection. Transient transfection offers a desirable safety profile, without the worry of cell persistence, tumorigenicity, and the like.

In summary, MSC have unique abilities that enable their use as a novel vaccine delivery method. These include (1) protection from allogeneic host responses (GvHD), (2) ease of production attributes including ability to be expanded and modified ex vivo for transient or stable transfection before in vivo administration, (3) ability to act as delivery vehicle/depot for antigen release over several days, and (4) initiation and possibly direct stimulation of antigen specific immune responses to these antigens in vivo.

The MSC platform described herein is capable of expressing hundreds of proteins, thereby generating a broad array of epitopes with correct post-translational processing, mimicking natural infection. By stimulating immunity to a combination of epitopes, prophylactic and even therapeutic vaccines to major global health diseases, like HIV, can be provided, where traditional vaccination approaches have failed.

The following non-limiting examples are provided to illustrate certain features and aspects of the methods described herein.

EXAMPLE 1

Figure 4:
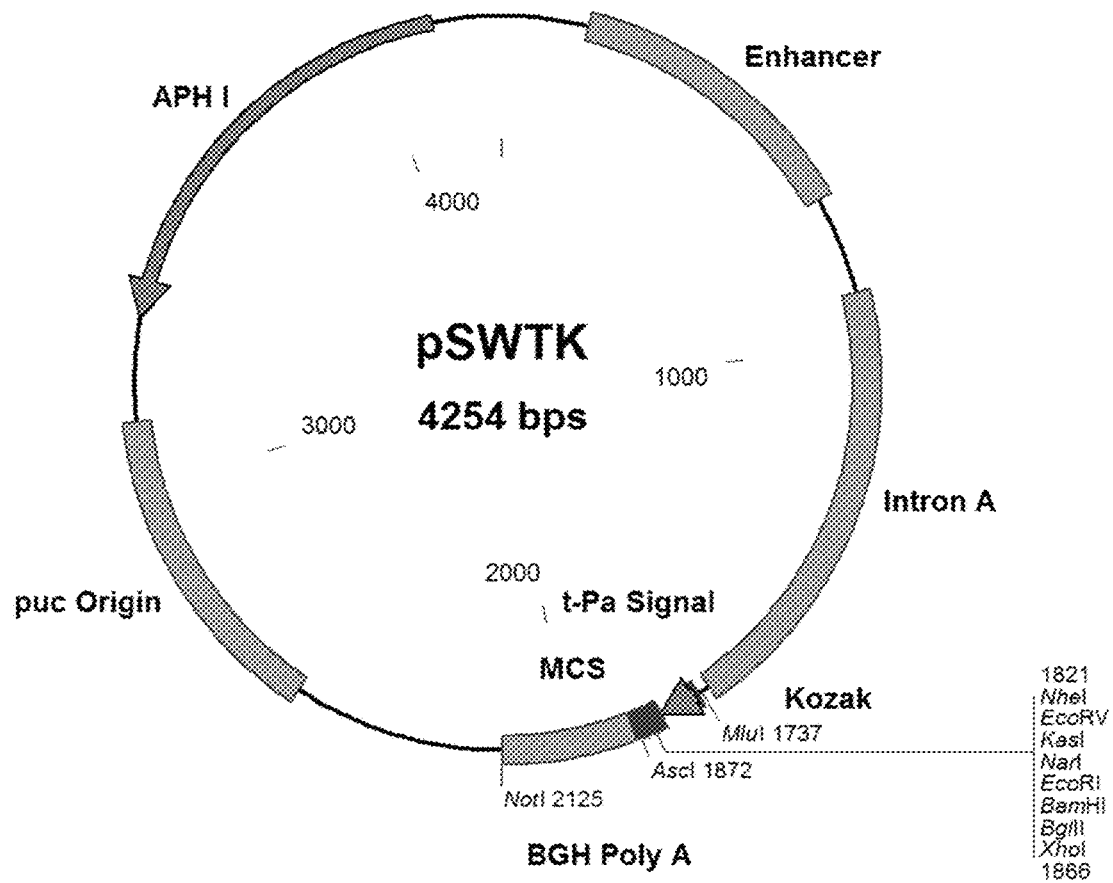
FIG. 4 provides a plasmid map of the pSWTK vector.

MSC derived from the bone marrow of C57Bl/6 mice were isolated and validated by the Tulane Center for Stem Cell Research and Regenerative Medicine (New Orleans, La.) as previously described (Ripoll and Bunnell, 2009). A total of $1 \times 10^6$ MSC were transfected by electroporation according to the manufacturer's instructions using the Invitrogen NEON system (Carlsbad, Calif.) with 2.5, 5 or 7.5 µg of a plasmid vector encoding gp120 (referred to herein as pSWTK-gp120) or empty vector (referred to herein as pSWTK), generously provided by Dr. V. S. Kalyanaraman of ABL Inc., Kensington, Md. FIG. 4 provides a plasmid map for the pSWTK vector, showing the schematic layout of the plasmid, including the insertion sites for the antigen. FIG. 5 provides the amino acid sequence of gp120 (SEQ ID NO: 1) encoded by the gene incorporated in the plasmid vector. 1. PCR fragments and the empty pSWTK plasmid (pSWTK-Empty) (restricted and unrestricted), were run on a E-GEL 2% agarose gel (Invitrogen) for 13 minutes. PCR fragments were generated from PLATINUM PCR SUPERMIX HF (Invitrogen), and TB-Forward and TB-Reverse primers. TB Forward had the sequence ATGCGCTAGCACGGATGT-GAGCCGGAAG (SEQ ID NO: 2), and TB Reverse had the sequence ACTAGGATCCTTAGCCGGCTCCGAGGCT-GCT (SEQ ID NO: 3). The PCR fragments and pSWTK-Empty were restricted with NheI for 2 hours at 37° C., then with BamHI for 2 hours at 37° C. The restricted PCR fragment and pSWTK-Empty were purified using PCR Purifiation Kit (Invitrogen) and ligated with T4 DNA Ligase (New England Biolabs), transformed into TOP10 cells (Invitrogen), and grown for 1 hour in LB+50 m/mL Kanamycin. Colonies were selected from an LB Agar+50 µg/mL Kanamycin plate and PCR analyzed using PLATINUM PCR SUPERMIX HF (Invitrogen) and TB-Forward and TB-Reverse primers. Colonies with correct inserts were grown overnight in LB+50 m/mL Kanamycin and purified using QIAPREP SPIN MINIPREP Kit (Qiagen). Clones 1, 3, and 7 were analyzed by PCR and restriction enzyme digestion and were sequenced by a commercial sequencing vendor. Clones 3 and 7 were determined to have the proper insert. pSWTK-TB.7 was transformed into TOP10 and D5α cells, grown up, and purified using HISPEED PLASMID MAXI KIT (Qiagen).

Panel A of FIG. 2 shows Gp120 immunofluorescence staining of MSC transfected with 5 µg pSWTK or pSWTK-gp120 1 or 7 days post-transfection, and controls using secondary(2°) antibody only, was carried out as previously described at 63X (Tomchuck et al., 2008). FIG. 2, Panel B, shows Western blot analysis of corresponding cell lysates (approximately 25 µg of protein) were probed with anti-gp120 as previously described (LaMarca et al., 2008). About $1 \times 10^5$ transfected MSC were incubated 1-4 days and the harvested cell culture supernatants were analyzed by an HIV-1 gp120 ELISA according to the manufacturer's instructions (ABL Inc.). FIG. 2, Panel C provides the HIV-1 gp120 ELISA results. Data are presented as the mean±standard error of the mean and analyzed by one-way ANOVA using the Tukey's post hoc test (GRAPHPAD PRISM Version 4). Statistical significance was determined by comparing pSWTK-gp120 and pSWTK groups. *$p<0.05$; $p<0.01$; *$p<0.001$.

EXAMPLE 2

Groups of 5 female C57Bl/6 mice (about 6-8 weeks old) underwent a single immunization with about 1×10$^6$ MSC transfected with about 7.5 μg pSWTK-gp120 (MSC-gp120) 16 hours post-transfection or 5 μg purified gp120, with naïve mice serving as a control. MSC and gp120 were diluted in DPBS and administered with a 0.5 mL syringe to deliver 100 μL per dose for intraperitoneal and subcutaneous injection, or 50 μL per dose for intramuscular injection. Mice were sacrificed 17 days post-immunization and sera collected. An ELISA for serum anti-gp120 IgG antibodies was performed as previously described (Norton et al., 2011). The ELISA results are provided in FIG. 3, graphed as 405 nm absorbance versus sera dilution (MSC-gp120 immunization results shown as solid lines; gp120 vector immunized mice, without MSC, shown as broken lines). Animal studies were approved by the Tulane University Institutional Animal Care and Use Committee.

The results shown in FIG. 3 clearly and surprisingly demonstrate significant antibody response from the mice immunized with the transfected MSC relative to mice treated with the protein (which elicited little or no antibody response). Subcutaneous and intramuscular administration of the MSC provided the strongest antibody response in these tests.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The terms "consisting of" and "consists of" are to be construed as closed terms, which limit any compositions or methods to the specified components or steps, respectively, that are listed in a given claim or portion of the specification. In addition, and because of its open nature, the term "comprising" broadly encompasses compositions and methods that "consist essentially of" or "consist of" specified components or steps, in addition to compositions and methods that include other components or steps beyond those listed in the given claim or portion of the specification. Recitation of ranges of values herein are merely intended to serve as a shorthand method of referring individually to each separate value falling within the range, unless otherwise indicated herein, and each separate value is incorporated into the specification as if it were individually recited herein. All numerical values obtained by measurement (e.g., weight, concentration, physical dimensions, removal rates, flow rates, and the like) are not to be construed as absolutely precise numbers, and should be considered to encompass values within the known limits of the measurement techniques commonly used in the art, regardless of whether or not the term "about" is explicitly stated. All methods described herein can be performed in any suitable order unless otherwise indicated herein or otherwise clearly contradicted by context. The use of any and all examples, or exemplary language (e.g., "such as") provided herein, is intended merely to better illuminate certain aspects of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

The following references are incorporated herein by reference in their entirety.

Abraham, E. J., Kodama, S., Lin, J. C., Ubeda, M., Faustman, D. L., and Habener, J. F. (2004). Human pancreatic islet-derived progenitor cell engraftment in immunocompetent mice. *Am J Pathol* 164, 817-830.

Aggarwal, S., and Pittenger, M. F. (2005). Human mesenchymal stem cells modulate allogeneic immune cell responses. *Blood* 105, 1815-1822.

Bergfeld, S. A., and Declerck, Y. A. (2010). Bone marrow-derived mesenchymal stem cells and the tumor microenvironment. *Cancer metastasis reviews* 29, 249-261.

Bhargava, A., Mishra, D., Banerjee, S., and Mishra, P. K. (2012). Dendritic cell engineering for tumor immunotherapy: from biology to clinical translation. *Immunotherapy* 4, 703-718.

Bunnell, B. A., Betancourt, A. M., and Sullivan, D. E. (2010). New concepts on the immune modulation mediated by mesenchymal stem cells. *Stem Cell Res Ther* 1, 34.

Cavenaugh, J. S., Awi, D., Mendy, M., Hill, A. V., Whittle, H., and Mcconkey, S. J. (2011). Partially randomized, non-blinded trial of DNA and MVA therapeutic vaccines based on hepatitis B virus surface protein for chronic HBV infection. *PloS one* 6, e14626.

Chan, J. L., Tang, K. C., Patel, A. P., Bonilla, L. M., Pierobon, N., Ponzio, N. M., and Rameshwar, P. (2006). Antigen-presenting property of mesenchymal stem cells occurs during a narrow window at low levels of interferon-gamma. *Blood* 107, 4817-4824.

Chen, B., Hu, J., Liao, L., Sun, Z., Han, Q., Song, Z., and Zhao, R. C. (2009). Flk-1+ mesenchymal stem cells aggravate collagen-induced arthritis by up-regulating interleukin-6. *Clin Exp Immunol* 159, 292-302.

Chen, K., Wang, D., Du, W. T., Han, Z. B., Ren, H., Chi, Y., Yang, S. G., Zhu, D., Bayard, F., and Han, Z. C. (2010). Human umbilical cord mesenchymal stem cells hUC-MSCs exert immunosuppressive activities through a PGE2-dependent mechanism. *Clinical immunology* 135, 448-458.

Chen, X., Armstrong, M. A., and Li, G. (2006). Mesenchymal stem cells in immunoregulation. *Immunol Cell Biol* 84, 413-421.

Choi, J. J., Yoo, S. A., Park, S. J., Kang, Y. J., Kim, W. U., Oh, I. H., and Cho, C. S. (2008). Mesenchymal stem cells overexpressing interleukin-10 attenuate collagen-induced arthritis in mice. *Clin Exp Immunol* 153, 269-276.

Corcione, A., Benvenuto, F., Ferretti, E., Giunti, D., Cappiello, V., Cazzanti, F., Risso, M., Gualandi, F., Mancardi, G. L., Pistoia, V., and Uccelli, A. (2006). Human mesenchymal stem cells modulate B-cell functions. *Blood* 107, 367-372.

Di Nicola, M., Carlo-Stella, C., Magni, M., Milanesi, M., Longoni, P. D., Matteucci, P., Grisanti, S., and Gianni, A. M. (2002). Human bone marrow stromal cells suppress T-lymphocyte proliferation induced by cellular or non-specific mitogenic stimuli. *Blood* 99, 3838-3843.

Djouad, F., Fritz, V., Apparailly, F., Louis-Plence, P., Bony, C., Sany, J., Jorgensen, C., and Noel, D. (2005). Reversal of the immunosuppressive properties of mesenchymal stem cells by tumor necrosis factor alpha in collagen-induced arthritis. *Arthritis Rheum* 52, 1595-1603.

Francois, M., Romieu-Mourez, R., Stock-Martineau, S., Boivin, M. N., Bramson, J. L., and Galipeau, J. (2009). Mesenchymal stromal cells cross-present soluble exogenous antigens as part of their antigen-presenting cell properties. *Blood* 114, 2632-2638.

Franquesa, M., Hoogduijn, M. J., and Baan, C. C. (2012). The impact of mesenchymal stem cell therapy in transplant rejection and tolerance. *Current opinion in organ transplantation* 17, 355-361.

Gao, J., Dennis, J. E., Muzic, R. F., Lundberg, M., and Caplan, A. I. (2001). The dynamic in vivo distribution of bone marrow-derived mesenchymal stem cells after infusion. *Cells Tissues Organs* 169, 12-20.

Gotherstrom, C. (2007). Immunomodulation by multipotent mesenchymal stromal cells. *Transplantation* 84, S35-37.

Hung, S.-C., Yang, D.-M., Chang, C.-F., Lin, R.-J., Wang, J.-S., Low-Tone Ho, L., and Yang, W. K. (2004). Immortalization without neoplastic transformation of human mesenchymal stem cells by transduction with HPV16E6/E7 genes. *International Journal of Cancer* 110, 313-319.

Jankovic, D., Caspar, P., Zweig, M., Garcia-Moll, M., Showalter, S. D., Vogel, F. R., and Sher, A. (1997). Adsorption to aluminum hydroxide promotes the activity of IL-12 as an adjuvant for antibody as well as type 1 cytokine responses to HIV-1 gp120. *J Immunol* 159, 2409-2417.

Klinge, P. M., Harmening, K., Miller, M. C., Heile, A., Wallrapp, C., Geigle, P., and Brinker, T. (2011). Encapsulated native and glucagon-like peptide-1 transfected human mesenchymal stem cells in a transgenic mouse model of Alzheimer's disease. *Neuroscience letters* 497, 6-10.

Klopp, A. H., Spaeth, E. L., Dembinski, J. L., Woodward, W. A., Munshi, A., Meyn, R. E., Cox, J. D., Andreeff, M., and Marini, F. C. (2007). Tumor irradiation increases the recruitment of circulating mesenchymal stem cells into the tumor microenvironment. *Cancer Res* 67, 11687-11695.

Kumar, S., Nagy, T. R., and Ponnazhagan, S. (2010). Therapeutic potential of genetically modified adult stem cells for osteopenia. *Gene therapy* 17, 105-116.

Lamalle-Bernard, D., Munier, S., Compagnon, C., Charles, M.-H., Kalyanaraman, V. S., Delair, T., Verrier, B., and Ataman-Onal, Y. (2006). Coadsorption of HIV-1 p24 and gp120 proteins to surfactant-free anionic PLA nanoparticles preserves antigenicity and immunogenicity. *Journal of Controlled Release* 115, 57-67.

Lamarca, H. L., Dash, P. R., Vishnuthevan, K., Harvey, E., Sullivan, D. E., Morris, C. A., and Whitley, G. S. (2008). Epidermal growth factor-stimulated extravillous cytotrophoblast motility is mediated by the activation of PI3-K, Akt and both p38 and p42/44 mitogen-activated protein kinases. *Hum Reprod* 23, 1733-1741.

Le Blanc, K., and Mougiakakos, D. (2012). Multipotent mesenchymal stromal cells and the innate immune system. *Nature reviews. Immunology* 12, 383-396.

Le Blanc, K., and Ringden, O. (2007). Immunomodulation by mesenchymal stem cells and clinical experience. *J Intern Med* 262, 509-525.

Li, X., Lu, Y., Huang, W., Xu, H., Chen, X., Geng, Q., Fan, H., Tan, Y., Xue, G., and Jiang, X. (2006). In vitro effect of adenovirus-mediated human Gamma Interferon gene transfer into human mesenchymal stem cells for chronic myelogenous leukemia. *Hematological oncology* 24, 151-158.

Liang, J., Gu, F., Wang, H., Hua, B., Hou, Y., Shi, S., Lu, L., and Sun, L. (2010). Mesenchymal stem cell transplantation for diffuse alveolar hemorrhage in SLE. *Nature reviews. Rheumatology* 6, 486-489.

Lim, J. H., Lee, M. H., Yi, H. G., Kim, C. S., Kim, J. H., and Song, S. U. (2010). Mesenchymal stromal cells for steroid-refractory acute graft-versus-host disease: a report of two cases. *International journal of hematology* 92, 204-207.

Liu, X. J., Zhang, J. F., Sun, B., Peng, H. S., Kong, Q. F., Bai, S. S., Liu, Y. M., Wang, G. Y., Wang, J. H., and Li, H. L. (2009). Reciprocal effect of mesenchymal stem cell on experimental autoimmune encephalomyelitis is mediated by transforming growth factor-beta and interleukin-6. *Clin Exp Immunol* 158, 37-44.

Loebinger, M. R., and Janes, S. M. (2010). Stem cells as vectors for antitumour therapy. *Thorax* 65, 362-369.

Majumdar, M. K., Keane-Moore, M., Buyaner, D., Hardy, W. B., Moorman, M. A., Mcintosh, K. R., and Mosca, J. D. (2003). Characterization and functionality of cell surface molecules on human mesenchymal stem cells. *J Biomed Sci* 10, 228-241.

Martino, G., Franklin, R. J., Baron Van Evercooren, A., and Kerr, D. A. (2010). Stem cell transplantation in multiple sclerosis: current status and future prospects. *Nature reviews. Neurology* 6, 247-255.

Mccormick, A. L., Thomas, M. S., and Heath, A. W. (2001). Immunization with an Interferon-γ-gp120 Fusion Protein Induces Enhanced Immune Responses to Human Immunodeficiency Virus gp120. *Journal of Infectious Diseases* 184, 1423.

Meisel, R., Zibert, A., Laryea, M., Gobel, U., Daubener, W., and Dilloo, D. (2004). Human bone marrow stromal cells inhibit allogeneic T-cell responses by indoleamine 2,3-dioxygenase-mediated tryptophan degradation. *Blood* 103, 4619-4621.

Newman, R. E., Yoo, D., Leroux, M. A., and Danilkovitch-Miagkova, A. (2009). Treatment of inflammatory diseases with mesenchymal stem cells. *Inflammation & allergy drug targets* 8, 110-123.

Norton, E. B., Lawson, L. B., Freytag, L. C., and Clements, J. D. (2011). Characterization of a mutant *Escherichia coli* heat-labile toxin, LT(R192G/L211A), as a safe and effective oral adjuvant. *Clin Vaccine Immunol* 18, 546-551.

Ohtaki, H., Ylostalo, J. H., Foraker, J. E., Robinson, A. P., Reger, R. L., Shioda, S., and Prockop, D. J. (2008). Stem/progenitor cells from bone marrow decrease neuronal death in global ischemia by modulation of inflammatory/immune responses. *Proc Natl Acad Sci USA* 105, 14638-14643.

Palucka, K., and Banchereau, J. (2012). Cancer immunotherapy via dendritic cells. *Nature reviews. Cancer* 12, 265-277.

Panes, J., Ordas, I., and Ricart, E. (2010). Stem cell treatment for Crohn's disease. *Expert review of clinical immunology* 6, 597-605.

Phinney, D. G., and Prockop, D. J. (2007). Concise review: mesenchymal stem/multipotent stromal cells: the state of transdifferentiation and modes of tissue repair—current views. *Stem Cells* 25, 2896-2902.

Potian, J. A., Aviv, H., Ponzio, N. M., Harrison, J. S., and Rameshwar, P. (2003). Veto-like activity of mesenchymal stem cells: functional discrimination between cellular responses to alloantigens and recall antigens. *Journal of immunology* 171, 3426-3434.

Prockop, D. J. (2009). Repair of tissues by adult stem/progenitor cells (MSCs): controversies, myths, and changing paradigms. *Mol Ther* 17, 939-946.

Raffaghello, L., Bianchi, G., Bertolotto, M., Montecucco, F., Busca, A., Dallegri, F., Ottonello, L., and Pistoia, V. (2008). Human mesenchymal stem cells inhibit neutrophil apoptosis: a model for neutrophil preservation in the bone marrow niche. *Stem Cells* 26, 151-162.

Rasmusson, I., Le Blanc, K., Sundberg, B., and Ringden, O. (2007). Mesenchymal stem cells stimulate antibody secretion in human B cells. *Scand J Immunol* 65, 336-343.

Ren, C., Kumar, S., Chanda, D., Chen, J., Mountz, J. D., and Ponnazhagan, S. (2008). Therapeutic potential of mesenchymal stem cells producing interferon-alpha in a mouse melanoma lung metastasis model. *Stem Cells* 26, 2332-2338.

Ringden, O., Uzunel, M., Rasmusson, I., Remberger, M., Sundberg, B., Lonnies, H., Marschall, H. U., Dlugosz, A., Szakos, A., Hassan, Z., Omazic, B., Aschan, J., Barkholt, L., and Le Blanc, K. (2006). Mesenchymal stem cells for treatment of therapy-resistant graft-versus-host disease. *Transplantation* 81, 1390-1397.

Ripoll, C. B., and Bunnell, B. A. (2009). Comparative characterization of mesenchymal stem cells from eGFP transgenic and non-transgenic mice. *BMC Cell Biol* 10, 3.

Rubio, D., Garcia-Castro, J., Martin, M. C., De La Fuente, R., Cigudosa, J. C., Lloyd, A. C., and Bernad, A. (2005). Spontaneous human adult stem cell transformation. *Cancer research* 65, 3035-3039.

Sasaki, M., Radtke, C., Tan, A. M., Zhao, P., Hamada, H., Houkin, K., Honmou, O., and Kocsis, J. D. (2009). BDNF-hypersecreting human mesenchymal stem cells promote functional recovery, axonal sprouting, and protection of corticospinal neurons after spinal cord injury. *J Neurosci* 29, 14932-14941.

Schena, F., Gambini, C., Gregorio, A., Mosconi, M., Reverberi, D., Gattorno, M., Casazza, S., Uccelli, A., Moretta, L., Martini, A., and Traggiai, E. (2010). Interferon-gamma-dependent inhibition of B cell activation by bone marrow-derived mesenchymal stem cells in a murine model of systemic lupus erythematosus. *Arthritis and rheumatism* 62, 2776-2786.

Song, Y. S., Lee, H. J., Doo, S. H., Lee, S. J., Lim, I., Chang, K.-T., and Kim, S. U. (2012). Mesenchymal stem cells over-expressing hepatocyte growth factor (HGF) inhibit collagen deposit and improve bladder function in rat model of bladder outlet obstruction. *Cell Transplantation*, -.

Sotiropoulou, P. A., Perez, S. A., Gritzapis, A. D., Baxevanis, C. N., and Papamichail, M. (2006). Interactions between human mesenchymal stem cells and natural killer cells. *Stem Cells* 24, 74-85.

Spaeth, E., Klopp, A., Dembinski, J., Andreeff, M., and Marini, F. (2008). Inflammation and tumor microenvironments: defining the migratory itinerary of mesenchymal stem cells. *Gene Ther* 15, 730-738.

Stagg, J. (2007). Immune regulation by mesenchymal stem cells: two sides to the coin. *Tissue Antigens* 69, 1-9.

Sundin, M., Ringden, O., Sundberg, B., Nava, S., Gotherstrom, C., and Le Blanc, K. (2007). No alloantibodies against mesenchymal stromal cells, but presence of antifetal calf serum antibodies, after transplantation in allogeneic hematopoietic stem cell recipients. *Haematologica* 92, 1208-1215.

Tolar, J., Nauta, A. J., Osborn, M. J., Panoskaltsis Mortari, A., Mcelmurry, R. T., Bell, S., Xia, L., Zhou, N., Riddle, M., Schroeder, T. M., Westendorf, J. J., Mcivor, R. S., Hogendoorn, P. C. W., Szuhai, K., Oseth, L., Hirsch, B., Yant, S. R., Kay, M. A., Peister, A., Prockop, D. J., Fibbe, W. E., and Blazar, B. R. (2007). Sarcoma Derived from Cultured Mesenchymal Stem Cells. *STEM CELLS* 25, 371-379.

Tomchuck, S. L., Zwezdaryk, K. J., Coffelt, S. B., Waterman, R. S., Danka, E. S., and Scandurro, A. B. (2008). Toll-like receptors on human mesenchymal stem cells drive their migration and immunomodulating responses. *Stem Cells* 26, 99-107.

Traggiai, E., Volpi, S., Schena, F., Gattorno, M., Ferlito, F., Moretta, L., and Martini, A. (2008). Bone marrow-derived mesenchymal stem cells induce both polyclonal expansion and differentiation of B cells isolated from healthy donors and systemic lupus erythematosus patients. *Stem Cells* 26, 562-569.

Tso, G. H., Law, H. K., Tu, W., Chan, G. C., and Lau, Y. L. (2010). Phagocytosis of apoptotic cells modulates mesenchymal stem cells osteogenic differentiation to enhance IL-17 and RANKL expression on CD4+ T cells. *Stem Cells* 28, 939-954.

Uccelli, A., Moretta, L., and Pistoia, V. (2008). Mesenchymal stem cells in health and disease. *Nature reviews. Immunology* 8, 726-736.

Uccelli, A., Pistoia, V., and Moretta, L. (2007). Mesenchymal stem cells: a new strategy for immunosuppression? *Trends Immunol* 28, 219-226.

Wang, Y., Guo, Y., Wang, X., Huang, J., Shang, J., and Sun, S. (2011). Human serum amyloid P functions as a negative regulator of the innate and adaptive immune responses to DNA vaccines. *Journal of immunology* 186, 2860-2870.

Waterman, R. S., Tomchuck, S. L., Henkle, S. L., and Betancourt, A. M. (2010). A new mesenchymal stem cell (MSC) paradigm: polarization into a pro-inflammatory MSC1 or an Immunosuppressive MSC2 phenotype. *PloS one* 5, e10088.

Wei, H. J., Wu, A. T. H., Hsu, C. H., Lin, Y. P., Cheng, W. F., Su, C. H., Chiu, W. T., Whang-Peng, J., Douglas, F. L., and Deng, W. P. (2011). The Development of a Novel Cancer Immunotherapeutic Platform Using Tumor-targeting Mesenchymal Stem Cells and a Protein Vaccine. *Molecular Therapy*.

Wernicke, C. M., Grunewald, T. G., Juenger, H., Kuci, S., Kuci, Z., Koehl, U., Mueller, I., Doering, M., Peters, C., Lawitschka, A., Kolb, H. J., Bader, P., Burdach, S., and Von Luettichau, I. (2011). Mesenchymal stromal cells for treatment of steroid-refractory GvHD: a review of the literature and two pediatric cases. *International archives of medicine* 4, 27.

Yi, T., and Song, S. U. (2012). Immunomodulatory properties of mesenchymal stem cells and their therapeutic applications. *Archives of Pharmacal Research* 35, 213-221.

We claim:

1. Episomally transfected primary mesenchymal stems cells (ETP-MSC) which episomally and transiently express at least one polypeptide having a sequence of a natural antigen from a pathogenic organism, or having a sequence that differs from the natural antigen by one or more conservative amino acid substitutions and sharing at least 50% sequence identity with the sequence of the natural antigen; and wherein the ETP-MSC elicit an antibody response to the antigen when the ETP-MSC are administered to a subject.

2. The ETP-MSC of claim 1 wherein the ETP-MSC episomally express a plurality of the antigens.

3. The ETP-MSC of claim 1 wherein the ETP-MSC episomally express about 2 to about 500 of the antigens.

4. The ETP-MSC of claim 1 wherein the ETP-MSC episomally express antigens from a plurality of pathogens.

5. The ETP-MSC of claim 1 wherein the antigen is a polypeptide from a virus.

6. The ETP-MSC of claim 1 wherein the MSC do not express an immune regulatory or costimulatory molecule.

7. The ETP-MSC of claim 1 wherein the antigen comprises HIV-1 gp120.

8. The ETP-MSC of claim 1 wherein the antigen is a polypeptide from a virus selected from the group consisting of: adenoviruses; papillomaviruses; hepadnaviruses; parvoviruses; pox viruses; Epstein-Barr virus; cytomegalovirus (CMV); herpes simplex viruses; roseolovirus; varicella zoster virus; filoviruses; paramyxoviruses; orthomyxoviruses; rhabdoviruses; arenaviruses; coronaviruses; human enteroviruses; hepatitis A virus; human rhinoviruses; polio virus; retroviruses; rotaviruses; flaviviruses; hepaciviruses; and rubella virus.

9. A pharmaceutical composition comprising the ETP-MSC of claim 1 in a pharmaceutically acceptable carrier.

* * * * *

UNITED STATES PATENT AND TRADEMARK OFFICE
CERTIFICATE OF CORRECTION

PATENT NO. : 10,472,647 B2
APPLICATION NO. : 14/081740
DATED : November 12, 2019
INVENTOR(S) : Suzanne L. Tomchuck et al.

Page 1 of 1

It is certified that error appears in the above-identified patent and that said Letters Patent is hereby corrected as shown below:

In the Specification

Column 12, Line 37, delete "LB + 50 m/mL" and insert --LB + 50 µg/mL--.
Line 42, delete "LB + 50 m/mL" and insert --LB + 50 µg/mL--.

Signed and Sealed this
Twenty-fourth Day of November, 2020

Andrei Iancu
*Director of the United States Patent and Trademark Office*

SEQUENCE LISTING

<160> NUMBER OF SEQ ID NOS: 3

<210> SEQ ID NO 1
<211> LENGTH: 498
<212> TYPE: PRT
<213> ORGANISM: Homo sapiens

<400> SEQUENCE: 1

```
Met Gly Ala Arg Ala Ser Val Leu Ser Gly Gly Lys Leu Asp Lys Trp
 1               5                  10                  15

Glu Lys Ile Arg Leu Arg Pro Gly Gly Lys Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Ser Ser Glu Gly Cys Arg Gln Ile Leu Gly Gln Leu
    50                  55                  60

Leu Pro Ala Leu Lys Thr Gly Ser Glu Glu Leu Arg Ser Leu Tyr Asn
65                  70                  75                  80

Thr Val Ala Thr Leu Tyr Cys Val His Gln Arg Ile Glu Val Lys Asp
                85                  90                  95

Thr Lys Glu Ala Leu Glu Lys Ile Glu Glu Glu Gln Ala Lys Ser Lys
            100                 105                 110

Lys Lys Glu Ala Ala Ala Asp Thr Gly Asn Ser Ser Gln Val Ser Gln
        115                 120                 125

Asn Tyr Pro Ile Val Gln Asn Met Gln Gly Gln Met Val His Gln Ala
    130                 135                 140

Ile Ser Pro Arg Thr Leu Asn Ala Trp Val Lys Val Val Glu Glu Lys
145                 150                 155                 160

Ala Phe Ser Pro Glu Val Ile Pro Met Phe Ser Ala Leu Ser Glu Gly
                165                 170                 175

Ala Thr Pro Gln Asp Leu Asn Thr Met Leu Asn Thr Val Gly Gly His
            180                 185                 190

Gln Ala Ala Met Gln Met Leu Lys Glu Thr Ile Asn Glu Glu Ala Ala
        195                 200                 205

Glu Trp Asp Arg Leu His Pro Val His Ala Gly Pro Ile Ala Pro Gly
    210                 215                 220

Gln Met Arg Glu Pro Arg Gly Ser Asp Ile Ala Gly Thr Thr Ser Thr
225                 230                 235                 240

Leu Gln Glu Gln Ile Gly Trp Met Thr Asn Asn Pro Pro Ile Pro Val
                245                 250                 255

Gly Glu Ile Tyr Lys Arg Trp Ile Ile Leu Gly Leu Asn Lys Ile Val
            260                 265                 270

Arg Met Tyr Ser Pro Thr Ser Ile Leu Asp Ile Arg Gln Gly Pro Lys
        275                 280                 285

Glu Pro Phe Arg Asp Tyr Val Asp Arg Phe Tyr Lys Thr Leu Arg Ala
    290                 295                 300

Glu Gln Ala Ser Gln Glu Val Lys Asn Trp Met Thr Glu Thr Leu Leu
305                 310                 315                 320

Val Gln Asn Ala Asn Pro Asp Cys Lys Thr Ile Leu Lys Ala Leu Gly
                325                 330                 335

Pro Ala Ala Thr Leu Glu Glu Met Met Thr Ala Cys Gln Gly Val Gly
            340                 345                 350

Gly Pro Gly His Lys Ala Arg Val Leu Ala Glu Ala Met Ser Gln Val
        355                 360                 365
```

```
Thr Asn Pro Ala Thr Ile Met Met Gln Arg Gly Asn Phe Arg Asn Gln
    370             375             380

Arg Lys Ile Val Lys Cys Phe Asn Cys Gly Lys Glu Gly His Ile Ala
385             390             395                         400

Arg Asn Cys Arg Ala Pro Arg Lys Lys Gly Cys Trp Lys Cys Gly Lys
            405             410                 415

Glu Gly His Gln Met Lys Asp Cys Thr Glu Arg Gln Ala Asn Phe Leu
            420             425             430

Gly Lys Ile Trp Pro Ser Tyr Lys Gly Arg Pro Gly Asn Phe Leu Gln
            435             440             445

Ser Arg Pro Glu Pro Thr Ala Pro Pro Glu Lys Ser Phe Arg Phe Gly
    450             455             460

Glu Glu Thr Ala Thr Pro Ser Gln Lys Gln Glu Pro Ile Asp Lys Glu
465             470             475             480

Met Tyr Pro Leu Thr Ser Leu Arg Ser Leu Phe Gly Asn Asp Pro Ser
                485             490             495

Ser Gln

<210> SEQ ID NO 2
<211> LENGTH: 28
<212> TYPE: DNA
<213> ORGANISM: Artificial Sequence
<220> FEATURE:
<223> OTHER INFORMATION: PCR primer

<400> SEQUENCE: 2
atgcgctagc acggatgtga gccggaag                                    28

<210> SEQ ID NO 3
<211> LENGTH: 31
<212> TYPE: DNA
<213> ORGANISM: Artificial Sequence
<220> FEATURE:
<223> OTHER INFORMATION: PCR primer

<400> SEQUENCE: 3
actaggatcc ttagccggct ccgaggctgc t                                31
```